United States Patent
Hasson

[11] Patent Number: 5,540,675
[45] Date of Patent: Jul. 30, 1996

[54] SUPPORT FOR SURGICAL INSTRUMENT

[76] Inventor: Harrith M. Hasson, 2043 N. Sedgwick, Chicago, Ill. 60614

[21] Appl. No.: 383,613

[22] Filed: Feb. 2, 1995

Related U.S. Application Data

[63] Continuation of Ser. No. 945,237, Sep. 15, 1992, abandoned.

[51] Int. Cl.$^6$ .................................................. A61B 19/00
[52] U.S. Cl. .............................. 606/1; 606/108; 606/130
[58] Field of Search ........................... 128/747, DIG. 26; 604/96–99, 102, 103, 158, 164, 165, 171–180, 264, 278; 606/1, 108, 130, 190–198, 184, 185

[56] References Cited

U.S. PATENT DOCUMENTS

| | | | |
|---|---|---|---|
| 3,893,446 | 7/1975 | Miller | 128/D26 |
| 3,961,632 | 6/1976 | Moossun | 128/D26 |
| 4,493,707 | 1/1985 | Ishihara | 604/164 |
| 4,883,053 | 11/1989 | Simon | 606/130 |
| 5,002,557 | 3/1991 | Hasson | 604/42 |
| 5,030,223 | 7/1991 | Anderson et al. | 606/130 |
| 5,056,523 | 10/1991 | Hotchkiss et al. | 606/130 |
| 5,100,411 | 3/1992 | Koutrovelis | 606/130 |
| 5,147,316 | 9/1992 | Castillenti | 604/164 |
| 5,176,697 | 1/1993 | Hasson et al. | 606/191 |
| 5,183,464 | 2/1993 | Dubrul et al. | 606/108 |
| 5,201,742 | 4/1993 | Hasson | 606/130 |
| 5,215,531 | 6/1993 | Maxson et al. | 604/180 |
| 5,263,956 | 11/1993 | Nobles | 606/130 |

FOREIGN PATENT DOCUMENTS

| | | | |
|---|---|---|---|
| 1680085 | 9/1991 | U.S.S.R. | 606/130 |

*Primary Examiner*—Michael H. Thaler
*Assistant Examiner*—Glenn Dawson
*Attorney, Agent, or Firm*—Wood, Phillips, VanSanten, Clark & Mortimer

[57] ABSTRACT

A support for a surgical instrument which support has a first sleeve with a through bore to allow passage of the instrument through the sleeve bore and tissue into a cavity in which a surgical procedure is to be performed and defining an outer surface to be pressed against the tissue, and structure for stabilizing the position of the sleeve relative to tissue through which the instrument is directed. There is connecting structure acting between the stabilizing structure and sleeve.

19 Claims, 2 Drawing Sheets

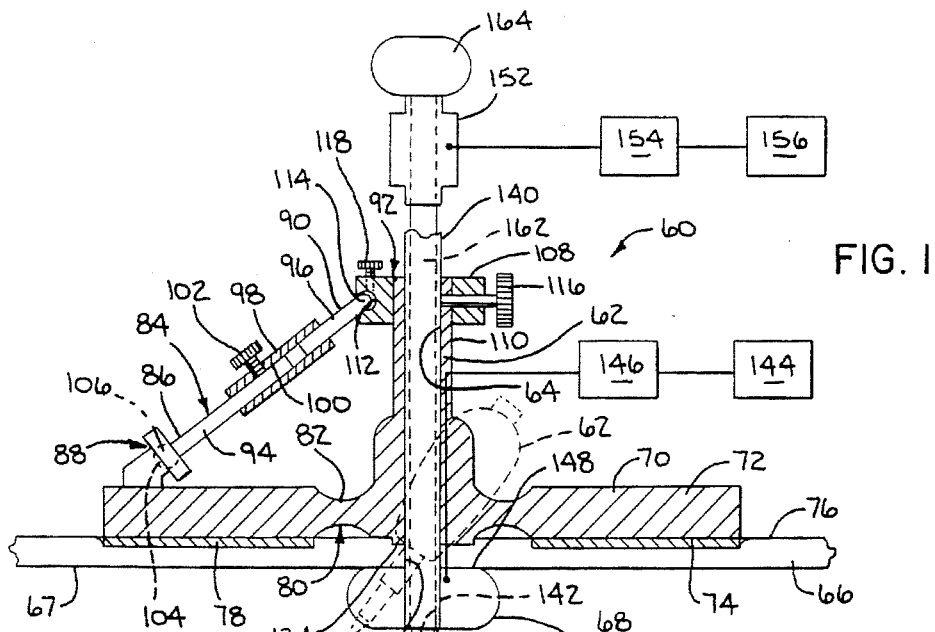
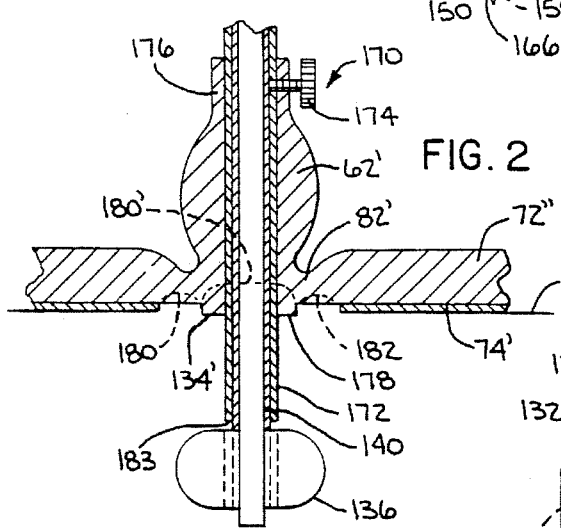
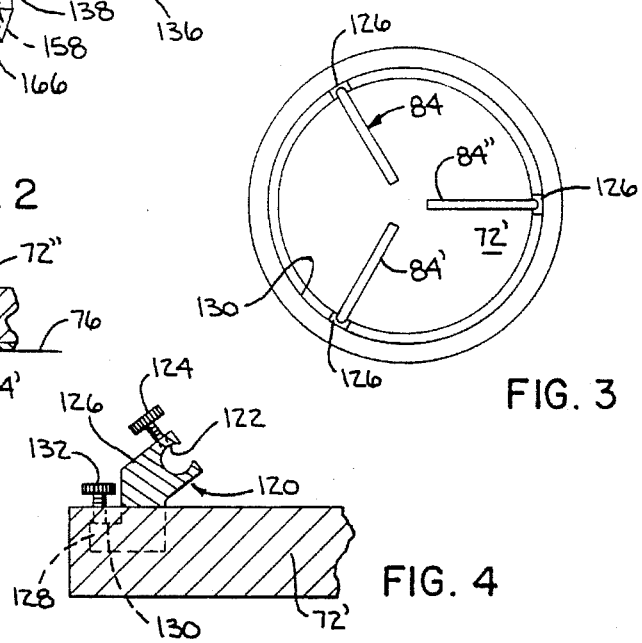
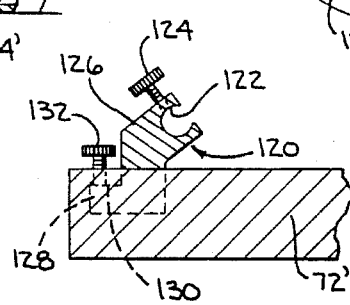
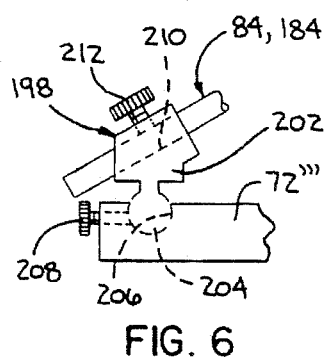
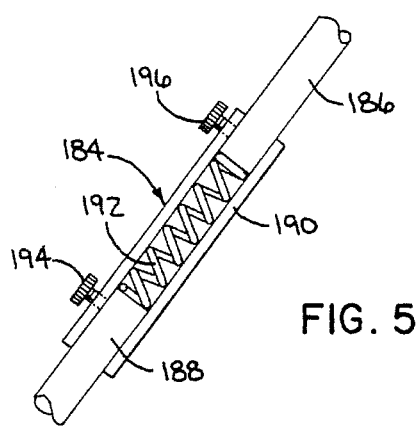
FIG. 1
FIG. 2
FIG. 3
FIG. 4
FIG. 5
FIG. 6

SUPPORT FOR SURGICAL INSTRUMENT

This application is a continuation of application Ser. No. 07/945,237, filed Sep. 15, 1992, now abandoned.

BACKGROUND OF THE INVENTION

1. Field of the Invention

This invention relates to surgical instruments and, more particularly, to a support for a laparoscopic surgical instrument to maintain a desired orientation of the instrument relative to a tissue through which the instrument extends.

2. Background Art

In performing laparoscopic surgery, an incision is made in a patient to admit a cannula which serves as a conduit for the introduction of selected surgical instruments into a body cavity. The body cavity in which the operation is performed is filled with a gas to distend the surrounding tissue to create a suitably sized operating space.

The inventor herein has designed structures to maintain the gas in the body cavity while allowing freedom of tilting movement for the surgical instrument. One such structure is shown in U.S. Pat. No. 5,002,557. This particular structure utilizes an elongate sleeve having an inflatable bladder at its distal end which is passed through the tissue into the body cavity. A collar with a conical sealing surface is slidable lengthwise of the sleeve. The distal end of the sleeve is passed through the tissue with the bladder deflated. Inflation of the bladder creates an annular shoulder which can be drawn up sealingly against the inside tissue surface. The collar is pressed into the tissue towards the bladder shoulder so that the bladder shoulder and collar captively embrace the tissue to thereby hold the sleeve in an operative position. The conical collar surface and bladder maintain a seal at the tissue incision even with the sleeve reoriented in use.

While the above structure affords a high integrity seal through a wide range of movement for the sleeve, it has one limitation. The basic instrument in U.S. Pat. No. 5,002,557 does not have any structure for maintaining a desired orientation of the sleeve. This feature is desirable to perform many conventional procedures. It is common to align the sleeve opening with a site at which more than one procedure is to be performed. The surgeon is usually required to remove and reinsert the same or different instruments. In the absence of some type of aligning structure for the sleeve, the surgeon is required to constantly manipulate the sleeve to access the same site. This is an inconvenience and time consuming. Further, certain procedures require the use of multiple instruments directed through separate incisions into a body cavity. The freely movable sleeves may reposition to cause interference between the various instruments therewithin. Furthermore, the conical structure limits the degree to which the sleeve can be tilted as the large end of the cone impinges on the opposing surface of the skin on the side to which the instrument is tilted.

The inventor herein has also developed certain guide structures in the form of adjustable jigs that can cooperate with an instrument such as that in U.S. Pat. No. 5,002,557. Exemplary structures are shown in co-pending application Ser. No. 686,149 entitled "Support Jig for a Surgical Instrument".

SUMMARY OF THE INVENTION

The present invention is specifically directed to overcoming the above-enumerated problems in a novel and simple manner.

More specifically, the present invention is directed to a support for a surgical instrument, which support has a first sleeve with a through bore to allow passage of the instrument through the sleeve bore and tissue into a cavity in which a surgical procedure is to be performed and defining an outer surface to be pressed against the tissue, and structure for stabilizing the position of the sleeve relative to the tissue through which the instrument is directed. There is connecting structure acting between the stabilizing structure and sleeve.

In one form, the sleeve and stabilizing and connecting structures are integrally formed as a single piece. With this one-piece construction, the support can be simply and economically constructed.

In one form, the stabilizing structure is a plate with a flat surface for facially engaging a tissue with the support in an operative position.

The connecting structure preferably allows relative movement between the sleeve and stabilizing structure. In a one-piece construction, the connecting structure can be defined by a deformable material that flexes to allow the required relative movement between the sleeve and stabilizing structure.

In a preferred form, the first sleeve and stabilizing structure are interconnected so as to define a deformable portion that acts as a hinge to allow universal relative movement between the stabilizing structure and sleeve.

The invention further contemplates the provision of structure connecting between the stabilizing structure and sleeve to maintain the sleeve and stabilizing structure in a desired relationship.

In one form, the maintaining structure is at least one member/rod that is extensible to alter the effective length of the member between the stabilizing structure and sleeve. In a more preferred form, a plurality of such elongate members are provided.

In one form, the extensible member(s) can be placed selectively in a) a first position wherein it has a first effective length and b) a second position wherein it has a second effective length. The extensible member(s) is normally biased towards one of its first and its second effective lengths.

In one form, the extensible member has spaced ends and at least one of the spaced ends is connected to one of the first sleeve and stabilizing structure to allow universal relative movement relative thereto.

In one form, there is structure for releasably holding the one member at a predetermined effective length.

In one form, the member(s) is attached to the stabilizing structure at a first location with the first location being changeable.

The invention further contemplates the above structure in combination with a guide sleeve/cannula defining a passageway to guide an instrument through a tissue into a cavity in which a surgical procedure is to be performed.

The invention further contemplates the ability to fix the relative positions of the first and guide sleeves.

In one form, a plastic sleeve surrounds at least a portion of the guide sleeve and is located between the guide sleeve and first sleeve. The plastic sleeve is secured, as by adhesive, to one of the guide and first sleeves.

The invention further contemplates the above structure in combination with a resilient, inflatable element to captively hold a tissue in conjunction with the stabilizing structure.

BRIEF DESCRIPTION OF THE DRAWINGS

FIG. 1 is a sectional elevational view of a surgical instrument support according to the present invention in operative relationship to a tissue;

FIG. 2 is a view as in FIG. 1 and showing a modified form of surgical instrument support according to the present invention;

FIG. 3 is a schematic plan view of a surgical instrument support according to the present invention utilizing three extensible members for maintaining the orientation of a sleeve for an instrument on the support;

FIG. 4 is a fragmentary, partial cross-sectional view of a universal connection for an end of one of the extensible members;

FIG. 5 is a fragmentary, partial cross-sectional view of one form of extensible member that is normally biased to a predetermined length;

FIG. 6 is a fragmentary, perspective view of a modified form of universal connection for an end of one of the extensible members.

DETAILED DESCRIPTION OF THE DRAWINGS

Figure 7:
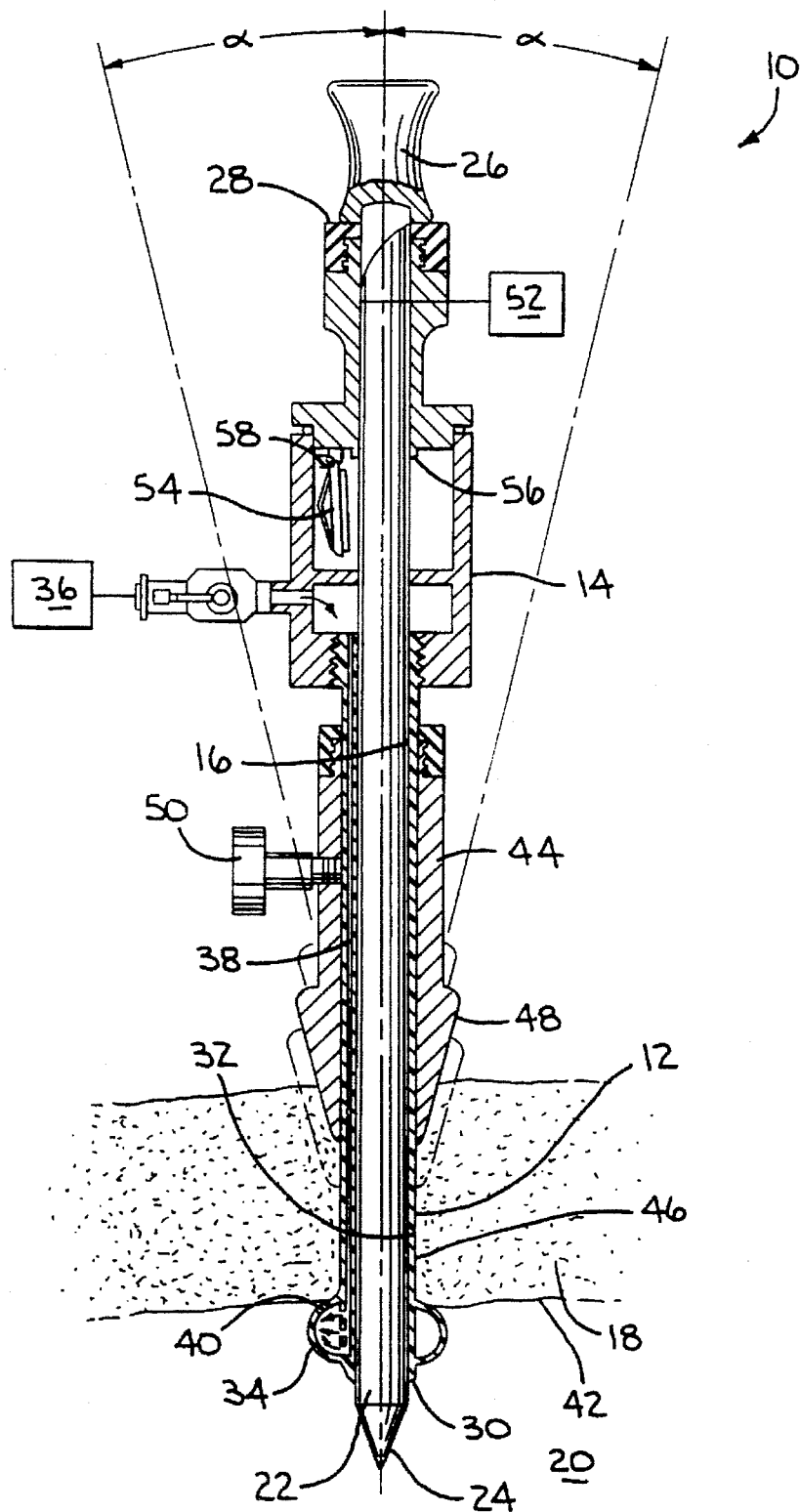
FIG. 7 is a sectional view of a prior art surgical instrument support in operative relationship to a tissue.

In FIG. 7, a prior art surgical instrument support is shown at 10. The support 10 has a sleeve 12 and housing 14 which cooperatively define a passageway 16 for a surgical instrument through a body tissue 18 into a cavity 20. A spike 22 with a sharpened distal end 24 is directed through the passageway 16 until an enlarged head 26 thereon abuts a shoulder 28 at the top of the housing 14. In this position, the sharpened distal end 24 protrudes from the free end 30 of the sleeve 12. The projecting, sharpened distal end 24 facilitates insertion of the instrument support 10 through a small incision 32 in the tissue 18.

The free end 30 of the sleeve 12 is advanced through the tissue 18 sufficiently that a bladder 34 thereon is fully exposed within the cavity 20. The bladder 34 is in a collapsed state as the sleeve 12 is directed through the tissue 18. Thereafter, the bladder 34 is inflated to the FIG. 7 configuration by fluid from a pressurized supply 36 which communicates through a passageway 38 integrally formed with the sleeve 12. The inflated bladder 34 defines an annular shoulder 40 which bears on the inside surface 42 of the tissue 18 to thereby prevent withdrawal of the sleeve 12 from the incision 32.

A collar 44 surrounds the sleeve 12 and is guided along the outer surface 46 thereof for movement lengthwise of the sleeve 12. The collar has a conical sealing surface 48 that can be pressed into the tissue 18. The surface 48 and surface 40 capture the tissue 18 and provide an effective seal around the incision 32. A set screw 50 can be tightened to lock the collar 44 to thereby maintain the instrument 10 in its operative position.

Once the collar 44 is locked, the spike 22 can be withdrawn. A gas, from a supply 52, can be introduced into the cavity 20 through the passageway 16 to distend the tissue 18 and define a suitable working area in the cavity 20. A hinged door 54 is abuttable to an annular shoulder 56 to seal the passageway 16. The door 54 is normally biased by a spring 58 into its sealing position. Entry of an instrument automatically pivots the door 54 into its open position shown in FIG. 7.

With the collar 44 locked in position, an effective seal is maintained by the sealing surface 48 and shoulder 40. This seal is maintained even as the sleeve 12 is tilted through a substantial angle, as indicated by the reference $\alpha$. However, due to the resilience of the tissue 18, there is nothing to effectively stabilize the orientation of the support 10 in any one position. This problem is solved by the inventive instrument support shown at 60 in FIG. 1.

The instrument support 60 consists of a sleeve 62 having a through bore 64 defining a passageway for the introduction of an instrument from externally of a tissue 66 therethrough into a cavity 68. The sleeve 62 has an integrally formed means 70 for stabilizing the position of the sleeve 62 relative to the tissue 66. The means 70 is in the form of an annular plate 72 having an annular, flat surface 74 for facially engaging the tissue 66 with the support in an operative position. The surface 74 may be borne directly against a tissue surface 76 or, alternatively, an adhesive layer 78 can be interposed between the surface 74 and tissue 66 to releasably hold the plate 72 in a desired position relative to the tissue 66. The plate has a diameter that is preferably at least 1 inch and a thickness of at least ⅛ inch.

A means at 80 connects the plate 72 to the sleeve 62. The connecting means 80 is preferably integrally formed with the sleeve 62 and plate 72 from a rubber, or other deformable material. The connecting means 80 has a reduced thickness to produce a universal-type hinge 82 between the sleeve 62 and plate 72. This hinge 82 allows the sleeve 62 to be tilted, with one exemplary tilt position shown in phantom lines in FIG. 1.

The invention further contemplates a means at 84 for maintaining the sleeve 62 and plate 72 in a desired relationship. The maintaining means 84 is in the form of an elongate, extensible member/rod having a first end 86 connected to the plate 72 through a connecting means 88 and a second end 90 connected to the sleeve 62 through a connecting means 92.

The extensible rod 84 is defined by first and second cooperating parts 94, 96, respectively. A mounting sleeve 98 has a through bore 100 to accept both the first rod part 94 and second rod part 96. The second rod part 96 is suitably fixed to the mounting sleeve 98, as by welding. The other rod part 94 is freely slidable in and out of the through bore 100 so as to thereby vary the effective length of the extensible rod 84. A set screw 102 fixes the rod part 94 relative to the mounting sleeve 98 to maintain a desired effective length for the rod 84.

The connecting means 88 includes a socket 104 for reception of a ball 106 integrally formed at the end of the rod part 94. The rod end 86 is thus free to move universally relative to the plate 72.

The connecting means 92 includes a collar 108 which surrounds the outer surface 110 of the sleeve 62. The collar 108 has a socket 112 therein to receive a ball 114 on the rod end 90 to allow universal pivoting of the rod end 90 relative to the collar 108. The collar 108 is slidable axially relative to the sleeve 62 and can be fixed in a desired position by a set screw 116.

Once the plate 72 is abutted to the tissue 66, the sleeve 62 can be reoriented to align the passageway 64 defined thereby with a site at which a procedure is to be performed. This adjustment is permitted with the set screw 102 loosened. When the desired orientation of the sleeve 62 is arrived at, the set screw 102 is tightened to thereby fix the effective length of the mounting rod 84. For purposes of stability, at least two additional, similarly constructed mounting rods 84', 84" are provided as shown in FIG. 3. This arrangement produces a tripod support which adds significant stability to the sleeve 62.

To further stabilize the sleeve 62, a set screw 118 is provided to lock the ball 114 in the socket 112 to thereby prevent inadvertent movement of the rod end 90. The rod end 86 can be suitably fixed using a modified form of connecting means 120 as shown in FIG. 4. The connecting means 120 includes a socket 122 for reception of the ball 106 and a set screw 124 to lock the ball 106 in the socket 122. A similarly locking mechanism can be provided on one or both of the additional rods 84', 84".

Additional versatility is afforded by providing a movable base 126 as part of the connecting means 88, as shown in FIGS. 3 and 4. The base 126 has an L-shaped leg 128 which is received in a guide slot 130 in a plate 72'. The slot 130 extends circumferentially about the plate 72' to allow the relative circumferential position of the base 126 to be selected relative to the plate 72'. The set screw 132 associated with each base 126 allows the position of each base 126 relative to the plate 72' to be fixed. Similar legs 128 can be provided on the other rods 84', 84".

Another aspect of the invention is the provision of a sealing surface 134 formed integrally with the sleeve 62 to provide a seal at the tissue incision. The sealing surface 134, which may have a reduced diameter or be slightly tapered to penetrate the tissue 6, performs a function similar to the sealing surface 48 on the collar 44 on the prior art support 10 in FIG. 7.

To enhance the seal of the sealing surface 134, an inflatable bladder 136 is provided at the distal end 138 of a cylindrical guide sleeve/cannula 140 that can be made part of or fit within the sleeve 62. The bladder 136 is collapsible against the peripheral surface 142 of the cannula 140 and inflatable by a fluid from a supply 144 through an appropriate conduit 146. The inflatable bladder 136 defines an annular shoulder 148 which, in conjunction with the sealing surface 134, captively holds the tissue 66 and seals around an incision 150 through which the cannula 140 extends. The sleeve 62 can be maintained in a desired position relative to the cannula 140 by the set screw 116 or by a separate set screw which allows independent adjustment of the sleeve 62 and cannula 140 and collar 108 and sleeve 62.

The cannula 140 is associated with a housing 152 which has means 154 thereon to allow introduction of gas from a supply 156 to and through a passageway 158 defined by the cannula 140 into the cavity 68.

To attach the support 60 to the tissue 66, the bladder 136 is initially deflated and the set screws 102, 116, 118, 124 and 132 loosened. A spike 162 with an enlarged head 164 is extended through the cannula passageway 158 to expose a sharpened tip 166 thereon at the distal end 138 of the cannula 140. The spike 162 and cannula 140 are then directed through the incision 150 until the bladder 136 is fully exposed in the cavity 68. Thereupon the bladder 136 is inflated to the configuration shown in FIG. 1. The cannula 140 is then pulled upwards until the inflated bladder 136 abuts the inside surface 67 of the tissue 66, anchoring the distal cannula end 138 inside the incision 150 and capturing the tissue 66 between the shoulder of the bladder 136 and the lower edge of the sealing surface 134 and lower surface 74 of the plate 72. The sleeve 62 is then slid down over the cannula 140 and squeezed against the tissue 66. The optional adhesive layer 78 firmly holds the plate 72 against the tissue 66. The orientation of the cannula 140 is then selected and maintained by tightening the several set screws 102, 116, 118, 124 and 132.

A modified form of support, according to the present invention, is shown at 170 in FIG. 2. The support 170 functions in the same manner as the support 60 and parts on the support 170 corresponding to those in the support 60 are similarly numbered in FIG. 2 including a "'" or a "''". In addition, a plastic or hard rubber sleeve 172 surrounds the cannula 140 and facilitates sliding movement of the sleeve 62' relative to the cannula 140. The plastic sleeve 172 is preferably adhered to one of the cannula 140 and sleeve 62'. The description below applies to the plastic sleeve 172 with the sleeve 172 adhered to the sleeve 62'. A set screw 174 extends through a reduced diameter portion 176 of the sleeve 62' and bears the plastic sleeve 172 frictionally against the cannula 140 to effect locking between the sleeve 62' and cannula 140.

The sleeve 62' is connected to a plate 72" through a hinge 82' as on the support 60. A projection 178 from the flat surface 74' of the plate 72" provides a reduced diameter sealing surface 134'. In this version, the projection 178 could be eliminated by extending the flat surface 74' in the same plane as shown by the dotted line 180 in FIG. 2 or the sleeve could be cut out as indicated by dotted lines 180'. In the former case, an annular undercut 182 in the surface 74' can be provided to facilitate the hinge action between the sleeve 62' and plate 72". The bladder 136 maintains the seal with the sleeve 62' with or without the projection 178.

The sleeve 172 also serves as an anchor to maintain the device within the incision. The sleeve 172 protrudes beyond the edge of the stabilizing plate 72" which impacts on the skin 76 by a fixed distance of about 6 mm. By releasing the set screw 174 and sliding the sleeves 62', 172 downward until the surface 74' of the plate 72" abuts the skin surface 76, the leading edge of sleeve 172 will automatically project approximately 6–10 mm through the skin incision. The sleeve 172 is 1 mm in thickness, and thus the outside diameter of the sleeve 172 is approximately 2 mm greater than that of the cannula 140, allowing the sleeve 172 to wedge firmly into the skin to thereby act as an anchor and a seal. It should be noted that the leading edge 183 of the sleeve 172 extends generally only into the incision and does not reach the balloon.

The sleeve 172 alone can be relied upon to maintain the seal around the incision without either the bladder 136 or projection 178. The sleeve 172 extends lengthwise of the cannula sufficiently with the support 170 in its operative position to maximize the contact area between the tissue 66 surrounding the incision and the sleeve 172. Thus, the sleeve 172 serves a dual purpose.

A still further modification contemplated by the present invention is shown in FIG. 5 for the extensible rod 184, which can be used for one or all of the rods 84, 84', 84". The rod 184 has first and second relatively movable parts 186, 188 extendable within a sleeve 190. A coil spring 192 within the sleeve 190 biases the rod parts 186, 188 away from each other to place the rod 184 in an extended state. With three sets of rods 184 mounted as in FIG. 3, the spring action 192 normally urges the sleeve 62, 62' into an upright state i.e. with the axis thereof at right angles to the plane of the surface 74, 74'. This obviates the user's having to manually maintain the sleeve 62, 62' upright as the cannula position is set. Set screws 194, 196 are provided to releasably fix the position of the rod parts 186, 188 relative to the sleeve 190.

FIG. 6 shows a modified form of universal connection at 198 between an end of one of the rods 84, 184 and a modified form of plate 72'''. The connection 198 includes a fitting 202 with an integral ball 204 that fits within a correspondingly configured recess 206 in the plate 72''' to allow guided universal movement between the fitting 202 and plate 72'''. The fitting 202 can be locked by a set screw 208. The fitting 202 has a through bore 210 to allow the rod parts 94, 188 to be guided fully therethrough to extend the range of adjustment for the sleeve 62, 62'. A locking screw 212 allows the rod parts 94, 188 to be fixed to the fitting 202.

The foregoing disclosure of specific embodiments is intended to be illustrative of the broad concepts comprehended by the invention.

I claim:

1. A support for a surgical instrument, said support comprising:

a first sleeve having a through bore to allow passage of an instrument through the first sleeve bore and tissue into a cavity in which a surgical procedure is to be performed and defining a surface to be pressed against tissue with the support in an operative position thereon;

means for stabilizing the position of the first sleeve relative to a tissue through which a surgical instrument is directed, said first sleeve being pivotable relative to the stabilizing means;

means connecting the stabilizing means to the first sleeve to allow the first sleeve to be placed in a plurality of different positions relative to the stabilizing means; and means cooperating between the first sleeve and stabilizing means for selectively maintaining the first sleeve in each of the plurality of different positions relative to the stabilizing means, said connecting means being made at least partially from a deformable material that flexes to allow universal relative movement between the first sleeve and stabilizing means.

2. The surgical instrument support according to claim 1 wherein the surface to be pressed against tissue is tapered and the sleeve, stabilizing means, and connecting means are formed as a single piece.

3. The support for a surgical instrument according to claim 1 wherein the stabilizing means comprises a plate with a flat surface for facially engaging a tissue with the support in an operative position.

4. The support for a surgical instrument according to claim 1 in combination with a guide sleeve/cannula extending into the through bore on the first sleeve and defining a passageway to guide an instrument through a tissue into a cavity in which a surgical procedure is to be performed.

5. The support for a surgical instrument according to claim 4 including means cooperating between the first and guide sleeves for selectively fixing the relative positions of the first sleeve and guide sleeve.

6. The support for a surgical instrument according to claim 4 including a resilient element on said guide sleeve that is positionable selectively in a) an inflated state and b) a deflated state, said resilient element defining a shoulder to capture a tissue through which said guide sleeve extends against the stabilizing means.

7. The support for a surgical instrument according to claim 4 further including a plastic sleeve surrounding at least a portion of the guide sleeve/cannula and located between the guide sleeve/cannula and the first sleeve; and further comprising means for fixing the plastic sleeve to at least one of the guide sleeve/cannula and the first sleeve.

8. A support for a surgical instrument, said support comprising:

a first sleeve having a through bore to allow passage of an instrument through the first sleeve bore and tissue into a cavity in which a surgical procedure is to be performed and defining a surface to be pressed against tissue with the support in an operative position thereon;

means for stabilizing the position of the first sleeve relative to a tissue through which a surgical instrument is directed;

means for connecting the stabilizing means to the first sleeve, wherein the stabilizing means comprises a plate with a flat surface for facially engaging a tissue with the support in an operative position, wherein the connecting means comprises means for allowing relative movement between the sleeve and stabilizing means; and means connected between the stabilizing means and sleeve for maintaining the sleeve and stabilizing means in a desired relationship, wherein the maintaining means connects between the stabilizing means and first sleeve and comprises at least one member that is extensible to alter the effective length of the at least one member between said stabilizing means and first sleeve.

9. The support for a surgical instrument according to claim 8 wherein the one extensible member can be placed selectively in a) a first position wherein it has a first effective length and b) a second position wherein it has a second effective length and there are means for normally biasing the one extensible member towards one of its first and second effective lengths.

10. The support for a surgical instrument according to claim 8 wherein there are means for releasably fixing the one member to hold the one member at a predetermined effective length.

11. A support for a surgical instrument, said support comprising:

a first sleeve having a through bore to allow passage of an instrument through the first sleeve bore and tissue into a cavity in which a surgical procedure is to be performed and defining a surface to be pressed against tissue with the support in an operative position thereon;

means for stabilizing the position of the first sleeve relative to a tissue through which a surgical instrument is directed;

means for connecting the stabilizing means to the first sleeve, wherein the stabilizing means comprises a plate with a flat surface for facially engaging a tissue with the support in an operative position, wherein the connecting means comprises means for allowing relative movement between the sleeve and stabilizing means; and means connected between the stabilizing means and sleeve for maintaining the sleeve and stabilizing means in a desired relationship, wherein the maintaining means comprises a plurality of elongate between the stabilizing means and first sleeve such that one of the first and second ends on each elongate member connects to the stabilizing means and the other of the first and second ends on each elongate member connects to the first sleeve.

12. A support for a surgical instrument, said support comprising:

a first sleeve having a through bore to allow passage of an instrument through the first sleeve bore and tissue into a cavity in which a surgical procedure is to be performed and defining a surface to be pressed against tissue with the support in an operative position thereon;

means for stabilizing the position of the first sleeve relative to a tissue through which a surgical instrument is directed;

means for connecting the stabilizing means to the first sleeve, wherein the stabilizing means comprises a plate with a flat surface for facially engaging a tissue with the support in an operative position, wherein the connecting means comprises means for allowing universal relative movement between the first sleeve and stabilizing means; and means acting between the stabilizing means and first sleeve for maintaining the sleeve and stabilizing means in a desired relationship, wherein there are first means at a first location on the stabilizing means for connecting the maintaining means to the stabilizing means and there are cooperating means on the first connecting means and stabilizing means for selectively changing the position of the first connecting means from said first location to a second location.

13. A support for a surgical instrument, said support comprising:

a first sleeve having a through bore to allow passage therethrough of an instrument to be directed through a tissue into a cavity in which a surgical procedure is to be performed;

means for stabilizing the position of the first sleeve relative to a tissue through which a surgical instrument is directed and having a surface to facially abut a tissue;

means for connecting the stabilizing means to the first sleeve to allow the first sleeve to be pivoted relative to the stabilizing means and thereby placed in a plurality of different positions relative to the stabilizing means; and means for maintaining the first sleeve in a plurality of different positions relative to the stabilizing means, wherein at least a portion of each of the first sleeve, the stabilizing means and connecting means is formed as one piece.

14. The support for a surgical instrument according to claim 13 wherein the stabilizing means comprises an annular plate with an annular surface for facially engaging a tissue with the support in an operative position.

15. The support for a surgical instrument according to claim 13 including second means connecting between the stabilizing means and first sleeve for maintaining the first sleeve and stabilizing means in a desired relationship.

16. The support for a surgical instrument according to claim 1 wherein the connecting means comprises a deformable part on one of the first sleeve and stabilizing means that acts as a hinge to allow the first sleeve to move relative to the stabilizing means, said first sleeve having a thickened portion that is less flexible than the deformable part on the first sleeve and stabilizing means.

17. A support for a surgical instrument, said support comprising:

a first sleeve having a through bore to allow passage therethrough of an instrument to be directed through a tissue into a cavity in which a surgical procedure is to be performed;

means for stabilizing the position of the sleeve relative to a tissue through which a surgical instrument is directed;

means for connecting the stabilizing means to the sleeve, wherein the stabilizing means comprises an annular plate with an annular surface for facially engaging a tissue with the support in an operative position, wherein the connecting means comprises means for allowing relative movement between the sleeve and stabilizing means; and means connecting between the stabilizing means and sleeve for maintaining the sleeve and stabilizing means in a desired relationship, wherein the maintaining means comprises at least one member that is extensible to alter the effective length of the at least one member between said stabilizing means and the first sleeve.

18. The support for a surgical instrument according to claim 17 wherein the extensible member has spaced ends connected one each to the stabilizing means and first sleeve and there are means cooperating between one spaced end of the extensible member and one of the first sleeve and stabilizing means to allow universal relative movement between the one extensible member end and the one of the first sleeve and stabilizing means.

19. The support for a surgical instrument according to claim 17 including means for releasably fixing the one member to hold the one member at a predetermined effective length.

* * * * *